US009201057B2

(12) United States Patent
Peng et al.

(10) Patent No.: US 9,201,057 B2
(45) Date of Patent: *Dec. 1, 2015

(54) INTEGRATED NANOPORE AND PAUL TRAP MECHANISM FOR DNA CAPTURE AND MOTION CONTROL

(71) Applicant: International Business Machines Corporation, Armonk, NY (US)

(72) Inventors: Hongbo Peng, Yorktown Heights, NY (US); Gustavo A. Stolovitzky, Riverdale, NY (US); Deqiang Wang, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 377 days.

This patent is subject to a terminal disclaimer.

(21) Appl. No.: 13/738,315

(22) Filed: Jan. 10, 2013

(65) Prior Publication Data

US 2014/0131203 A1    May 15, 2014

Related U.S. Application Data

(63) Continuation of application No. 13/675,389, filed on Nov. 13, 2012.

(51) Int. Cl.
   *G01N 33/487*     (2006.01)
   *C12Q 1/68*      (2006.01)
   *B82Y 30/00*     (2011.01)

(52) U.S. Cl.
   CPC ........ *G01N 33/48721* (2013.01); *C12Q 1/6869* (2013.01); *B82Y 30/00* (2013.01)

(58) Field of Classification Search
   CPC .................. G01N 27/44791; G01N 27/4473; G01N 33/68; G01N 33/48721; C12Q 1/6869; C12Q 1/6825; C12Q 1/6813; C12Q 1/6876; Y10S 977/852; Y10S 977/733; Y10S 977/72; Y10S 977/721; B82Y 5/00; B82Y 15/00
See application file for complete search history.

(56) References Cited

U.S. PATENT DOCUMENTS

| | | | |
|---|---|---|---|
| 2004/0149580 A1* | 8/2004 | Flory | 204/518 |
| 2006/0073489 A1* | 4/2006 | Li et al. | 435/6 |
| 2008/0286750 A1* | 11/2008 | Xu et al. | 435/4 |
| 2011/0031389 A1* | 2/2011 | Reed et al. | 250/282 |
| 2011/0053284 A1* | 3/2011 | Meller et al. | 436/149 |

OTHER PUBLICATIONS

Yann Astier et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," JACS Articles; American Chemical Society; Published on web: Jan. 12, 2006; 128, 1705-1710; 6 pages.

(Continued)

*Primary Examiner* — Jennifer Dieterle
(74) *Attorney, Agent, or Firm* — Cantor Colburn LLP; Vazken Alexanian

(57) ABSTRACT

A mechanism is provided for capturing a molecule via an integrated system. An alternating voltage is applied to a Paul trap device in an electrically conductive solution to generate electric fields. The Paul trap device is integrated with a nanopore device to form the integrated system. Forces from the electric fields of the Paul trap device position the molecule to a nanopore in the nanopore device. A first voltage is applied to the nanopore device to capture the molecule in the nanopore of the nanopore device.

9 Claims, 9 Drawing Sheets

(56) References Cited

OTHER PUBLICATIONS

Daniel Branton et al., "The Potential and Challenges of Nanopore Sequencing," Nature Publishing Group; http://www.nature.com/naturebiotechnology; Published online Oct. 9, 2008; vol. 26, No. 10; 8 pages.

Donald J. Douglas et al., "Linear Ion Traps in Mass Spectrometry," Department of Chemistry, Published online in Wiley InterScience (www.interscience.wiley.com); Dec. 2003; 29 pages.

Jiunn B. Heng et al., "Sizing DNA Using a Nanometer-Diameter Pore," The Biophysical Society; Biophysical Journal; vol. 87; Oct. 2004; 2905-2911; 7 pages.

Sony Joseph et al., "A Long DNA Segment in a Linear Nanoscale Paul Trap," Nanotechnology 21 (2010); IOP Publishing; 11 pages.

John J. Kasianowicz et al., "Characterization of Individual Polynucleotide Molecules Using a Membrane Channel," Proc. Natl. Acad. Sci. USA; vol. 93, pp. 13770-13773, Nov. 1996; Biophysics; 4 pages.

Marcela Rincon-Restrepo et al., "Controlled Translocation of Individual DNA Molecules through Protein Nanopores with Engineered Molecular Brakes," ACS Publications; Nano Lett. 2011, 746-750; 5 pages.

\* cited by examiner

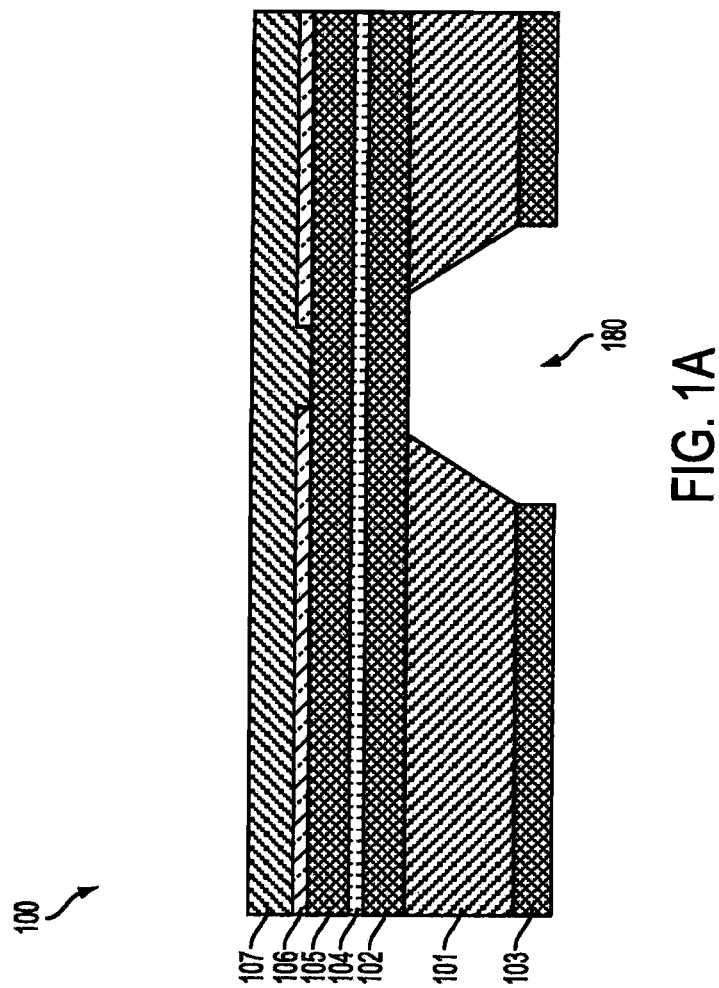

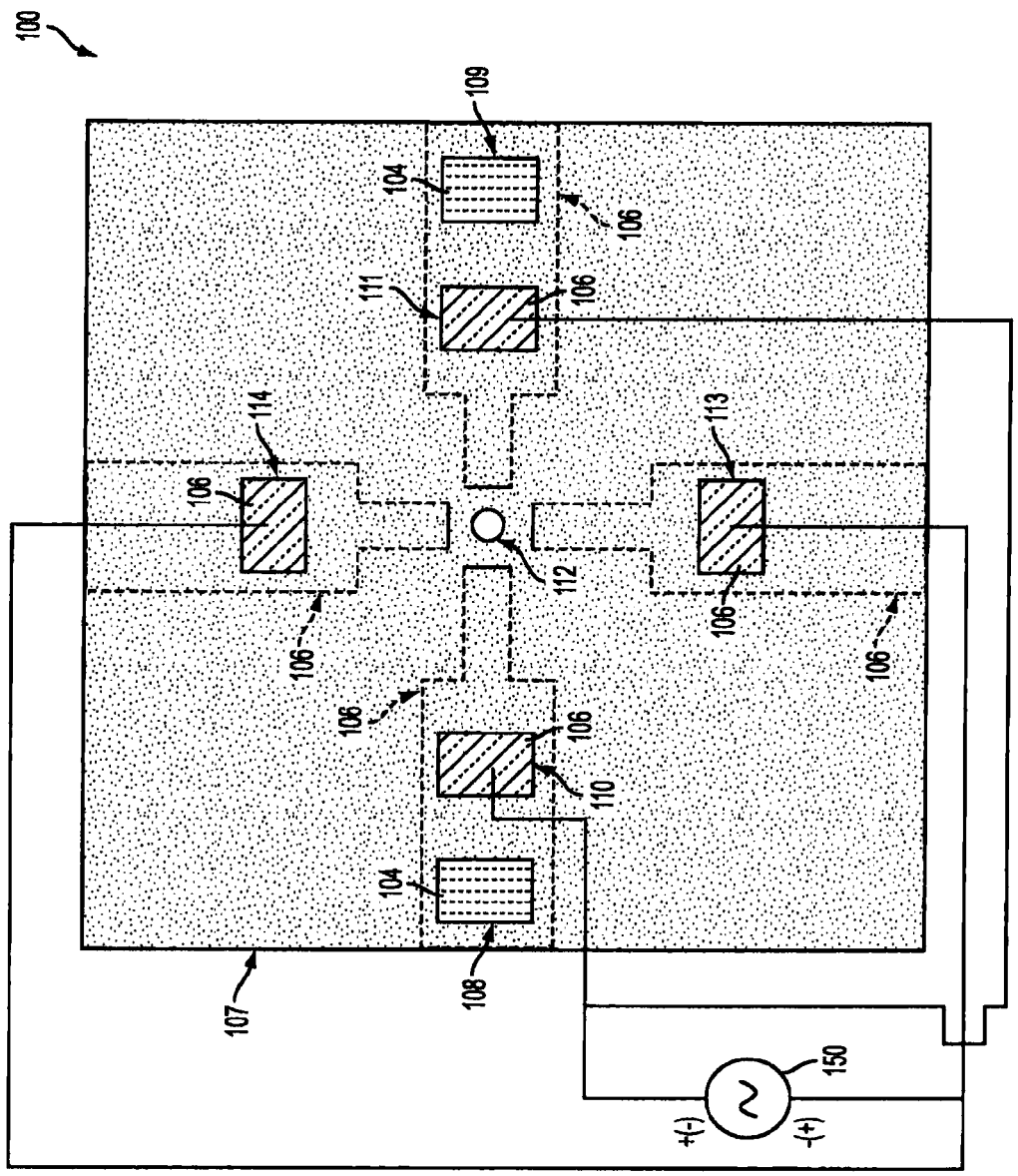

INTEGRATED NANOPORE AND PAUL TRAP MECHANISM FOR DNA CAPTURE AND MOTION CONTROL

CROSS-REFERENCE TO RELATED APPLICATIONS

This application is a continuation of U.S. Non-Provisional application Ser. No. 13/675,389, entitled "INTEGRATED NANOPORE AND PAUL TRAP MECHANISM FOR DNA CAPTURE AND MOTION CONTROL", filed Nov. 13, 2012, which is incorporated herein by reference in its entirety.

BACKGROUND

The present invention relates to nanopore devices, and more specifically, to capture and control of molecules in nanopore devices.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method is provided for capturing a molecule via an integrated system. The method includes applying an alternating voltage to a Paul trap device in an electrically conductive solution to generate electric fields, and the Paul trap device is integrated with a nanopore device to form the integrated system. Forces from the electric fields of the Paul trap device position the molecule to a nanopore in the nanopore device. The method includes applying a first voltage to the nanopore device to capture the molecule in the nanopore of the nanopore device.

According to an embodiment, a system for capturing a molecule is provided. The system includes a nanopore device including a nanopore and a Paul trap device integrated with the nanopore device to form an integrated system. An alternating voltage is applied to the Paul trap device in an electrically conductive solution to generate electric fields. Forces from the electric fields of the Paul trap device position the molecule to the nanopore in the nanopore device. The nanopore device has a first voltage applied to capture the molecule in the nanopore of the nanopore device.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1D illustrate views of fabricating a multilayer structure for making an integrated nanopore and linear Paul trap system according to an embodiment, in which:

FIG. 1A is a cross-sectional view of a multilayer structure for making an integrated nanopore and linear Paul trap system;

FIG. 1B is a cross-sectional view of the multilayer structure which shows the process to fabricate contact pads as conductive layers for sensing via the nanodevice and contact pads as conductive layers for the linear Paul trap device;

FIG. 1C is a cross-sectional view showing that a nanopore is made through the layers of the multilayer structure; and FIG. 1D is a top view of the multilayer structure showing contact pads for the nanodevice and contact pads for the linear Paul trap device, which are connected to an alternating current voltage source.

DETAILED DESCRIPTION

Figure 1B:
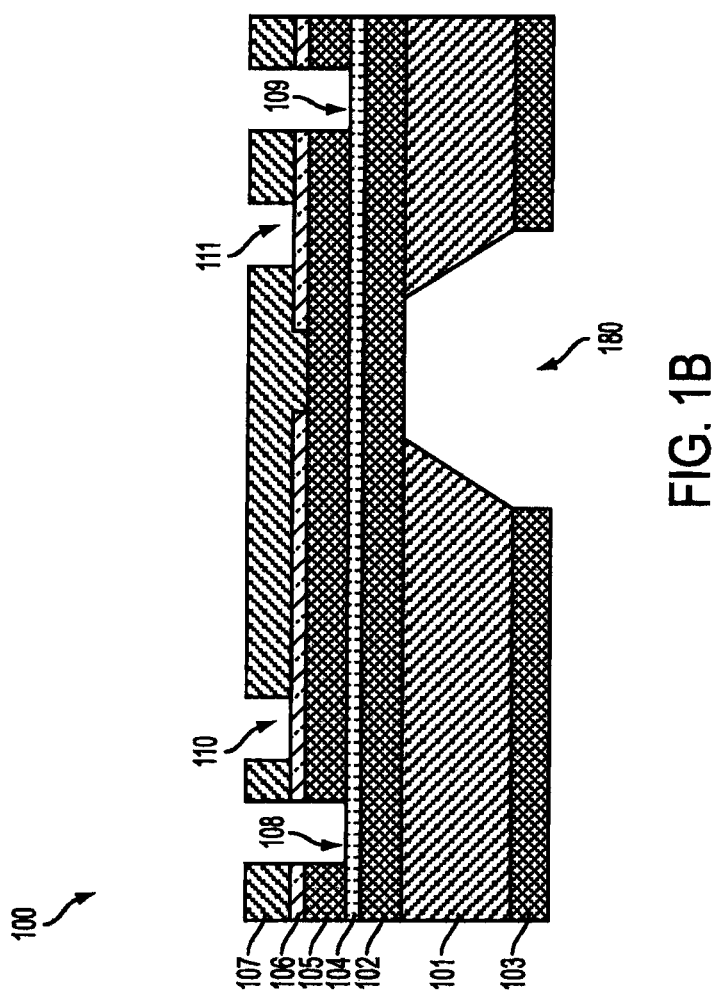

An embodiment provides a technique and a device to control DNA motion and enhance DNA capture rate into a nanopore by integrating the nanopore and linear Paul trap together in a liquid environment of electrically conductive solution. This nanodevice can be utilized for DNA and RNA sequencing.

The linear Paul trap is used in mass spectrometry to effectively trap single ion and charge molecules in a vacuum environment. In the embodiment, the linear Paul trap is utilized in the liquid environment to trap single long strand DNA molecules, which is one of the steps to sequence the whole genome.

Accordingly, an integrated nanopore and linear Paul trap system in a liquid environment is discussed herein. This system can trap the long strand DNA and/or RNA as well as enhance the capture rates of DNA and RNA into the nanopore. The linear Paul trap can capture and trap the single long strand DNA in certain range (e.g., in tens of nanometers). The nanopore (in nanometer size which is close to the diameter of DNA and RNA) can physically localize single strand DNA in the nanometer range, providing enough dwelling time for identifying single bases.

Now turning to the figures, FIG. 1A is a cross-sectional view of a multilayer structure 100 for making an integrated nanopore and linear Paul trap system. The multilayer structure 100 may include a substrate 101 such as silicon (Si) with 500 micrometer in thickness. The multilayer structure 100 includes electrically insulating films 102, 103, 105, and 107, and the insulating films may include silicon nitride ($Si_3N_4$). The thickness of them can vary from few to tens of nanometers. The insulating film 103 can be used as an etching mask for etching through the substrate 101 via either dry or wet etching to form the window 180, and the etching stops on layer 102. As a result, part of layer 102 will be a free-standing membrane. Layers 104 and 106 are electrically conductive layers separated by electrically insulating layer 105. The conductive layer 104 can be 0.3 to few nanometers in thickness. The thickness of 106 can be tens of nanometers, like 20 nanometers. The electrically conductive layers 104 and 106 are a metal such as titanium. The free-standing membrane part of 104 as described above is visible under a transmission electron microscope. To make a nanometer size nanopore, FIG. 1C is a cross-sectional view to show that a nanopore 112 is made through the layers 102, 104, 105, 106, and 107 via a transmission electron microscope, electron beam lithography, or other technologies.

Figure 1C:
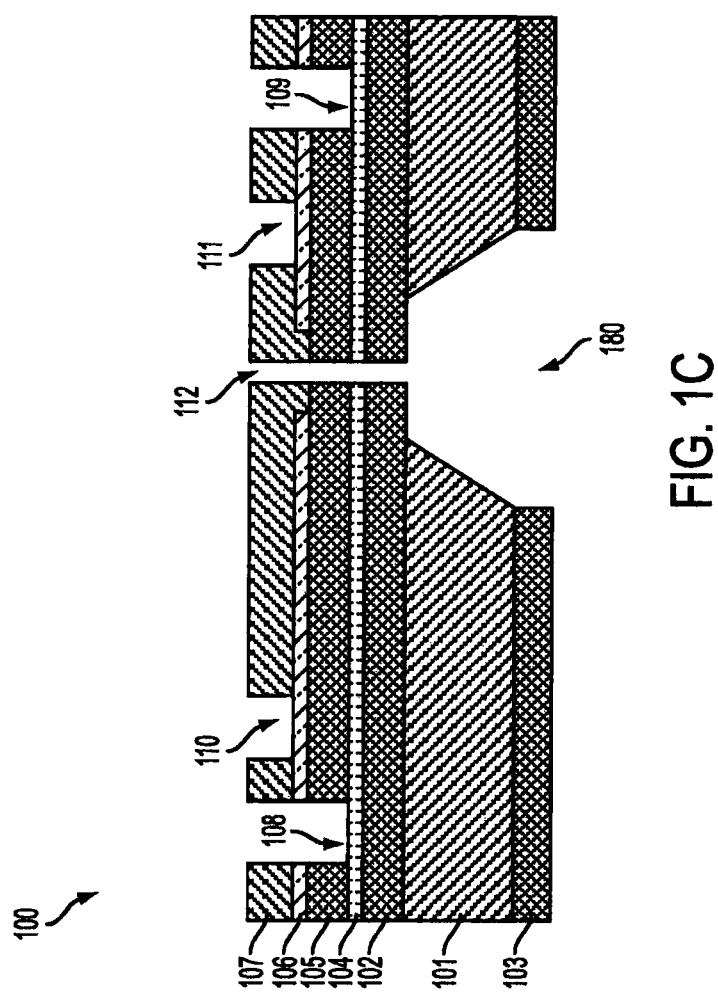

FIG. 1B is a cross-sectional view of the multilayer structure 100 which shows the process to fabricate contact pads as conductive layers 104 for sensing and conductive layer 106 for the linear Paul trap.

The windows (vias) 108 and 109 are opened through insulating layer 105, conductive layer 106, and insulating layer 107 down to the conductive layer 104 (metal), and the windows 108 and 109 are contact pads used for sensing the difference for base pairs of the DNA molecule inside nanopore 112 by impedance, current, and/or other technologies as understood by one skilled in the art. They can be 5 micrometers by 5 micrometers or up to hundreds of micrometers.

Windows 110, 111, 113, and 114 are the contact pads for the linear Paul trap system, and are opened down to conductive layer 106 (i.e., metal). Windows 113 and 114 are not shown in the cross-sectional view of FIG. 1B but are shown in the top view of FIG. 1D. The dimensions of them can be 5 micrometers by 5 micrometers or up to hundreds of micrometers.

FIG. 1D is a top view of the multilayer structure 100 showing contact pads 108 and 109 for operating the nanopore device and contact pads 110, 111, 113, and 114 for operating the linear Paul trap device.

Contact pads and windows may be used interchangeably because the metal is accessed through the open windows. The contact pads 110 and 111 are connected to the same polarity of an alternating current (AC) voltage source 150, and the contact pads 113 and 114 are connected to the same polarity of the alternating current (AC) voltage source 150 which is different from the contact pads 110 and 111.

Figure 2:
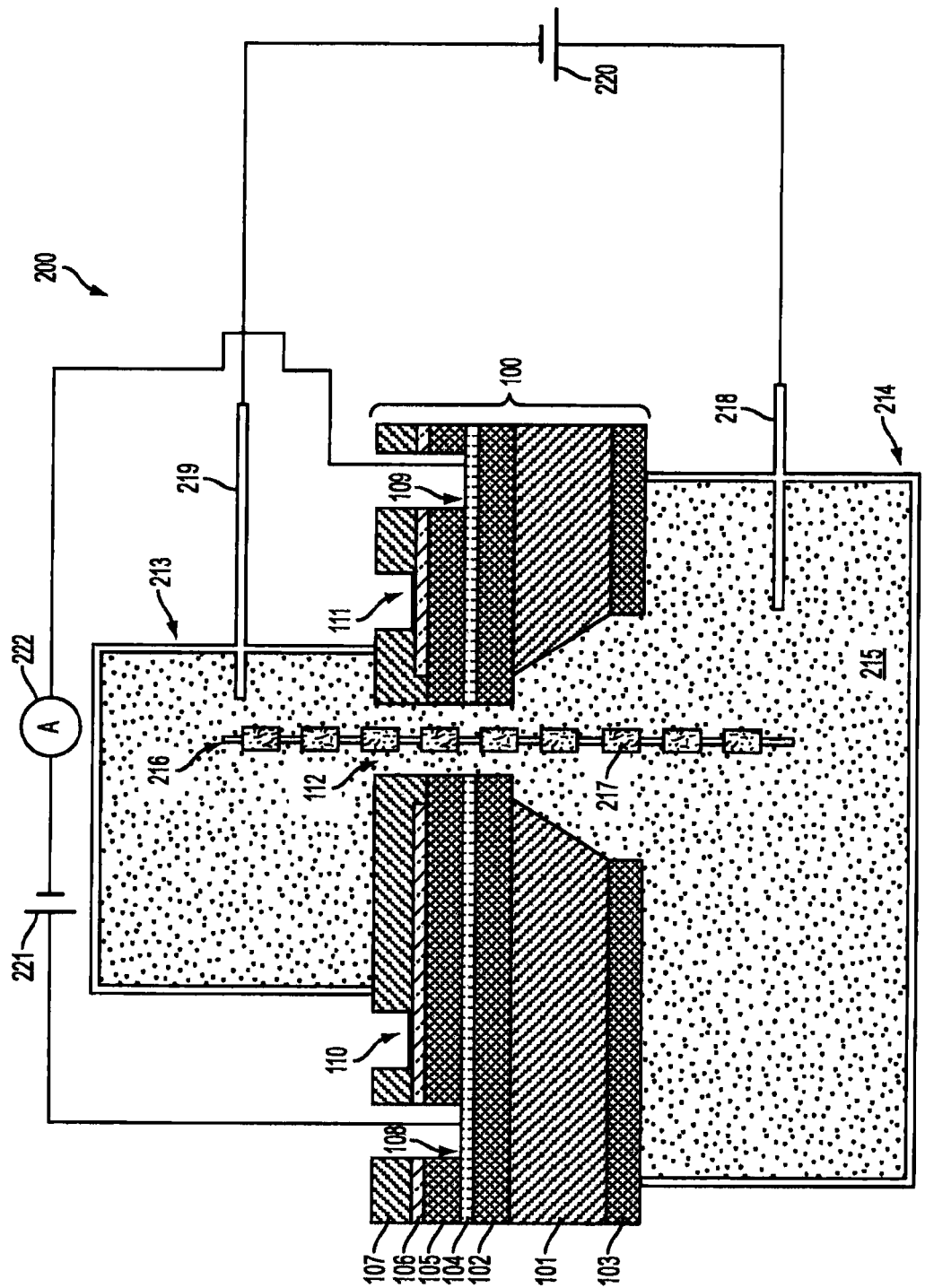
FIG. 2 is a cross-sectional view of the multilayer structure of the nanopore device and the linear Paul trap device in an integrated system.

In the embodiment, the insulating cap layer 107 is disposed so that the classical linear Paul trap system/device can work with electrically conductive solution 215 (shown in FIG. 2). The cap layer 107 covers/shields the conducting layer 106 from the electrically conductive solution 215 flowing in the nanopore 112 and protects the conducting layer 106 from shorting out in the electrically conductive solution 215 (i.e., blocks the circuit from being complete through the electrically conductive solution 215) when voltage is applied by the alternating current voltage source 150. In one instance, the positive signal $$\left(+\frac{1}{2}V_{rf}\cos(\omega_{rf}t)\right)$$

is applied to the conductive layer 106 in windows 110 and 111, while the negative signal $$\left(-\frac{1}{2}V_{rf}\cos(\omega_{rf}t)\right)$$

is applied to the conductive layer 106 in windows 113 and 114. The positive and negative signals (i.e., polarity) continue to alternate as understood by one skilled in the art. As applied by the AC voltage source 150, $V_{rf}$ is the amplitude of rf signal and $\omega_{rf}$ is the frequency of the rf signal.

FIG. 2 is a cross-sectional view of an integrated system/device 200 for capturing and sequencing molecules, such as DNA and RNA molecules. Particularly, FIG. 2 is a schematic of the multilayer structure 100 of the nanopore device and the linear Paul trap device in the integrated system 200. In the integrated system 200, elements 101 through 112 of the multilayer structure 100 are the same as discussed above.

The multilayer structure 100 in the integrated system 200 of the nanopore and Paul trap device separates the electrically conductive solution 215 into two reservoirs 213 and 214. The electrically conductive solution 215 is only connected through the nanopore 112 for the two reservoirs 213 and 214. Negatively charged DNA molecule 216 may be in the reservoir 213. The alternating voltage of the alternating voltage source 150 is applied to the conducting layer 106 of the contact pads 110 and 111 (with one polarity) and the contacting layer 106 of the contacts pads 113 and 114 (with another polarity); this produces a virtual focus point at the nanopore 112 which positions the DNA molecule 216 at the nanopore 112. (The connections of the (metal) contact pads 110, 111, 113, and 114 to the alternating voltage source 150 are not repeated in FIG. 2 so as not to obstruct the view but are understood to be present.) The negatively charged DNA molecule 216 can be pulled through the nanopore 112 by the voltage of a voltage source 220, and each base of the DNA molecule 216 is illustrated as base 217. The voltage of the voltage source 220 is applied between the two reservoirs 213 and 214 via two metal electrodes 218 and 219, for example Ag/AgCl. The voltage signal of the voltage source 221 is applied between the two sides of the conductive layer 104 through via widows 108 and 109. The current signals are detected by the current ammeter 222. When the DNA molecule 216 is detected inside nanopore 112, the linear Paul trap system traps the DNA molecule 216 inside the nanopore 112 by the alternating voltage of the alternating voltage source 150. So the DNA bases 217 can be sensed and identified through current measured by the ammeter 222 (and other technologies). In order to sequence the long strand DNA or RNA, the voltage pulse signal can be applied from voltage source 220 to move the DNA base 217 one by one out of the nanopore 112 after the DNA molecule 216 is immobilized.

Figure 5:
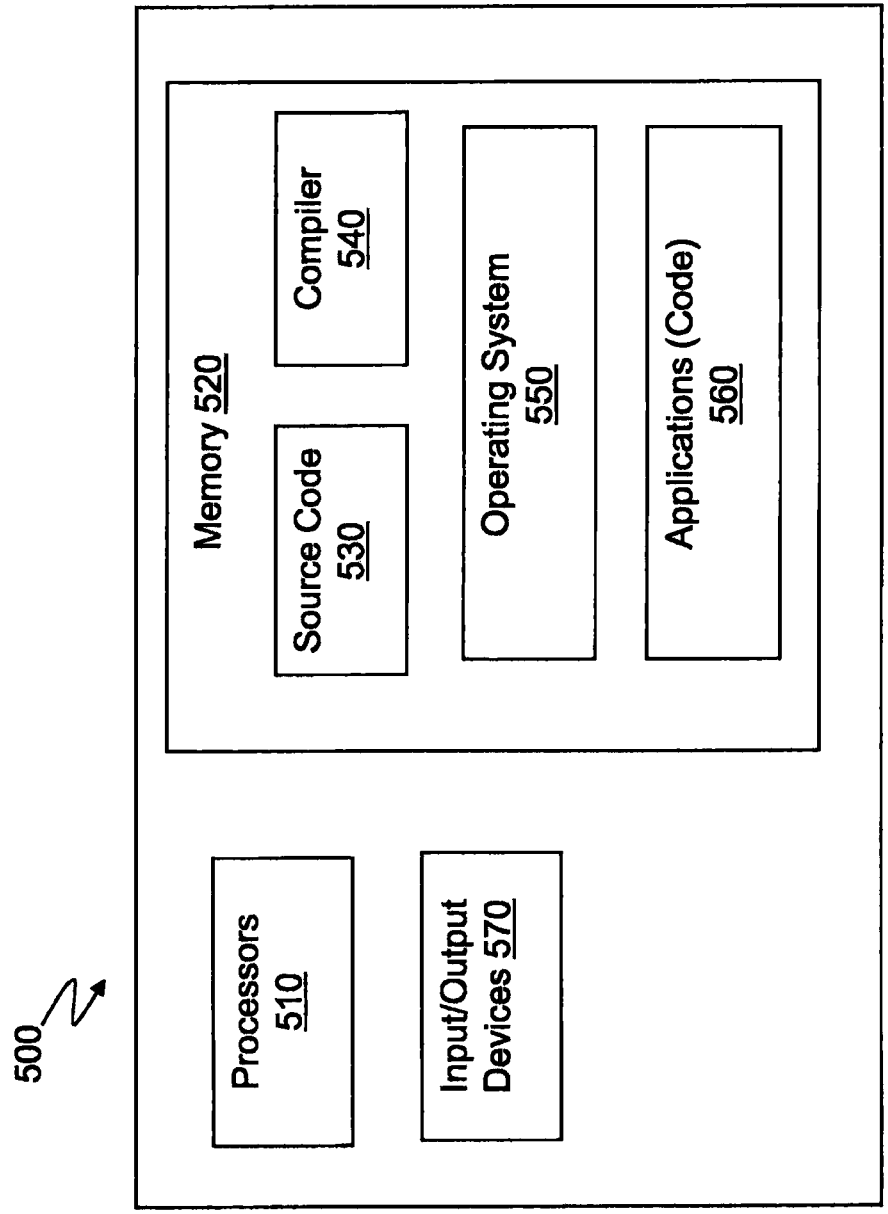
FIG. 5 is a block diagram that illustrates an example of a computer (computer setup) having capabilities, which may be included in and/or combined with embodiments.

While the molecule 216 is in nanopore 112, a change in the current (measured via ammeter 222 which may be connected to/implemented in a computer 500 in FIG. 5) is detected. The amount of change in the measured current depends on the size and surface charge of the respective bases 217 of the DNA molecule 216. In this way, each base 217 is sensed (i.e., sequenced) as it passes through nanopore 112 as understood by one skilled in the art.

Figure 3:
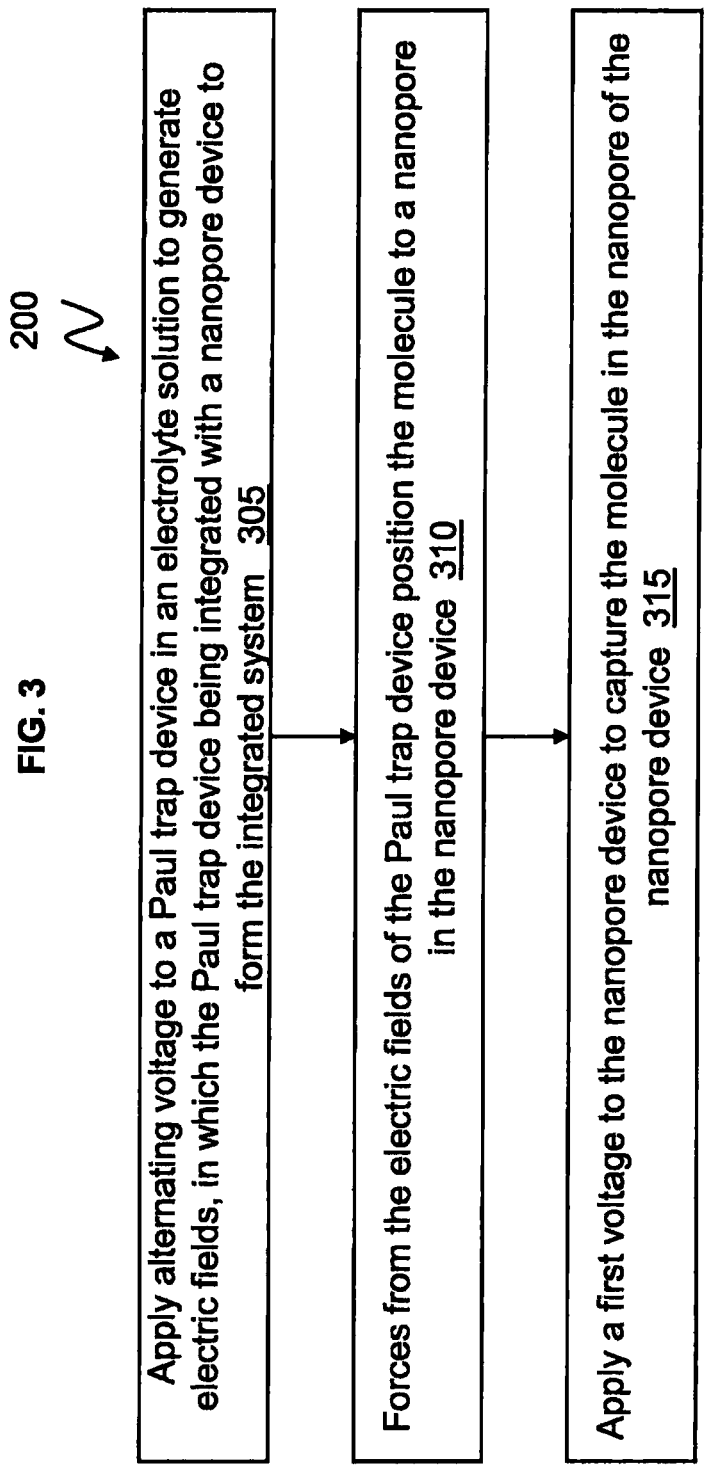
FIG. 3 is a method for capturing and sequencing molecules using the integrated system of the nanodevice and the Paul trap device.

FIG. 3 is a method 300 for capturing and sequencing molecules 216 using the integrated system 200 of the nanopore device and the Paul trap device.

At block 305, alternating voltage (also referred to as AC voltage) is applied by the AC voltage source 150 to a Paul trap device in an electrically conductive solution 215 (e.g., an electrolyte solution) to generate electric fields, and the Paul trap device is integrated within the nanopore device to form the integrated system.

While the molecule 216 is in the electrically conductive solution 215 of the reservoir 213 (assuming that the DNA molecules 216 are first pumped into the reservoir 213), forces from the electric fields of the Paul trap device position the molecule 216 to the nanopore 212 in the nanopore device at block 310.

A first voltage is applied (via electrodes 218 and 219) to the nanopore device by the voltage source 220 to capture the molecule 216 in the nanopore 112 of the nanopore device at the block 315.

The method includes applying a second voltage (via voltage source 221 connected to contact pads 108 and 109) to the nanopore device to sequence bases 217 of the molecule 216 in the nanopore 112.

The method in which the alternating voltage is applied (via AC voltage source 150 connected to contact pads 110, 111, 113, and 114) to the Paul trap device prior to applying the first voltage (of the voltage source 220) to the nanopore device.

The method in which the alternating voltage is applied to the Paul trap device while applying the first voltage to the nanopore device.

The method includes centering the molecule 216 to a location (e.g., the mouth of the nanopore 112 in the reservoir 213) of the nanopore 112 in the nanopore device by a combination of the forces of the Paul trap device (when alternating voltage of the AC voltage source 150 is applied to contact pads 110, 111, 113, and 114) and the first voltage applied by the voltage source 220 (via electrodes 218 and 219) to the nanopore device.

The method in which the Paul trap device comprises first pair of contact pads (also referred to as windows 110 and 111) and a second pair of contact pads (also referred to as windows 113 and 114), where the alternating voltage alternates polarity between the first pair of contact pads (which may have a positive polarity first then switch to a negative polarity) and the second pair of contact pads (which may have a negative polarity first then switch to a positive polarity). The electrically conductive solution 215 fills the two reservoirs (top reservoir 213 and bottom reservoir 214) connected by the nanopore 112. Insulating material layer 107 surrounds immersed parts of the first pair of contact pads (windows 110 and 111) and the second pair of contact pads (windows 113 and 114 shown in FIG. 1D) in the electrically conductive solution 215 to prevent the first pair of contact pads (windows 110 and 111 opening to conducting layer 106) and the second pair of contacts pads (windows 113 and 114 opening to conducting layer 106) from conducting electricity through the electrically conductive solution 215. Applying the alternating voltage (via the AC voltage source 150) to the first pair of contact pads and the second pair of contact pads positions the molecule 216 to the nanopore 112 in one of the two reservoirs (e.g., the top reservoir 213) for capture below in the nanopore 212. The forces, continuously changing (with the changing polarity of the AC voltage source 150), act upon the molecule 216 to force the molecule 216 into an equilibrium position centered at the nanopore 112, in order to prevent the molecule 216 from being moved out of position (out of position by being moved to the left or the right or out of position by being moved to the top or bottom (relative to FIG. 1D)). The first voltage is applied to one electrode (e.g., electrode 218) in one of the two reservoirs and another electrode (e.g., electrode 219) in another one of the two reservoirs. The first voltage moves the molecule 216 through the nanopore 112 for sequencing respective bases 217 of the molecule 216. The first voltage is turned off to sequence one base 217 and turned on again to move to a next base 217.

Figure 4A:
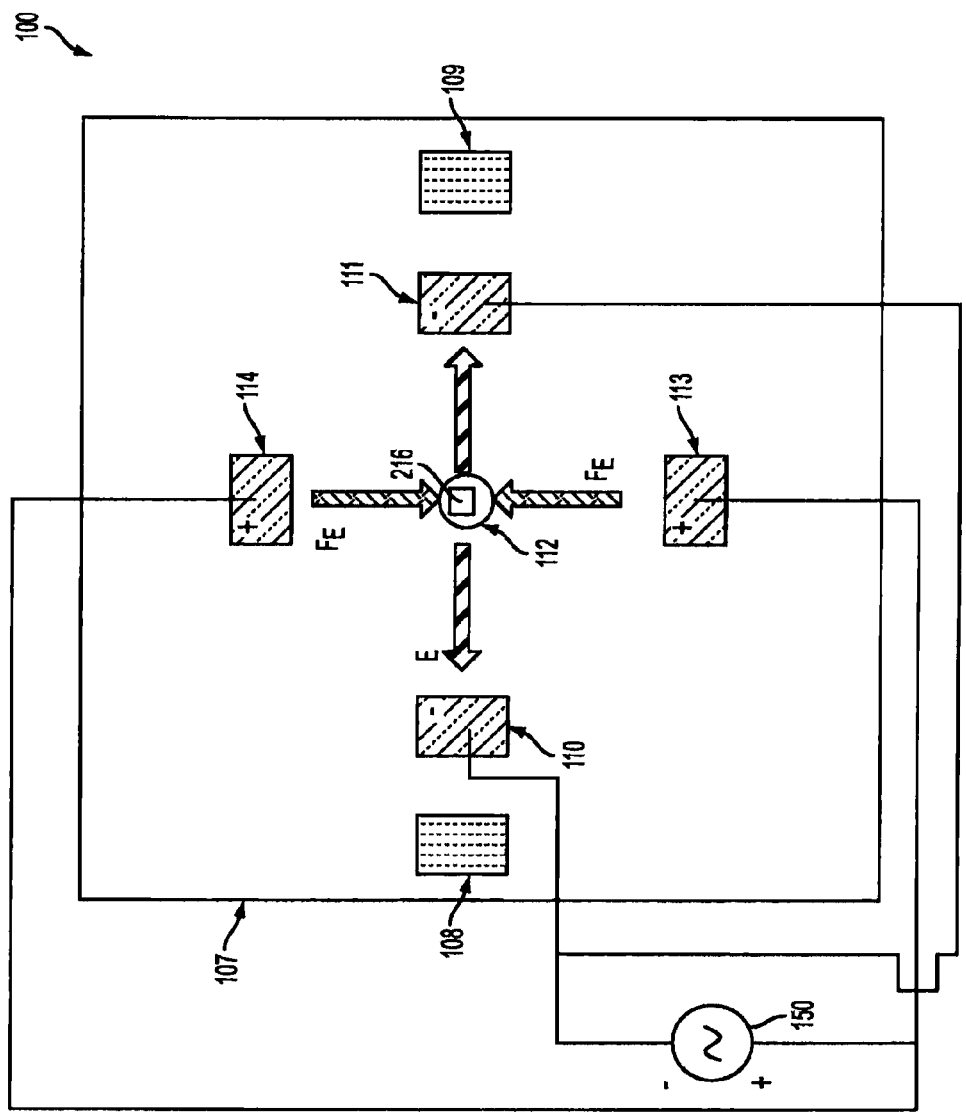
FIG. 4A illustrates how the Paul trap device positions and centers the molecule when voltage is applied with one polarity of the alternating current voltage source.
Figure 4B:
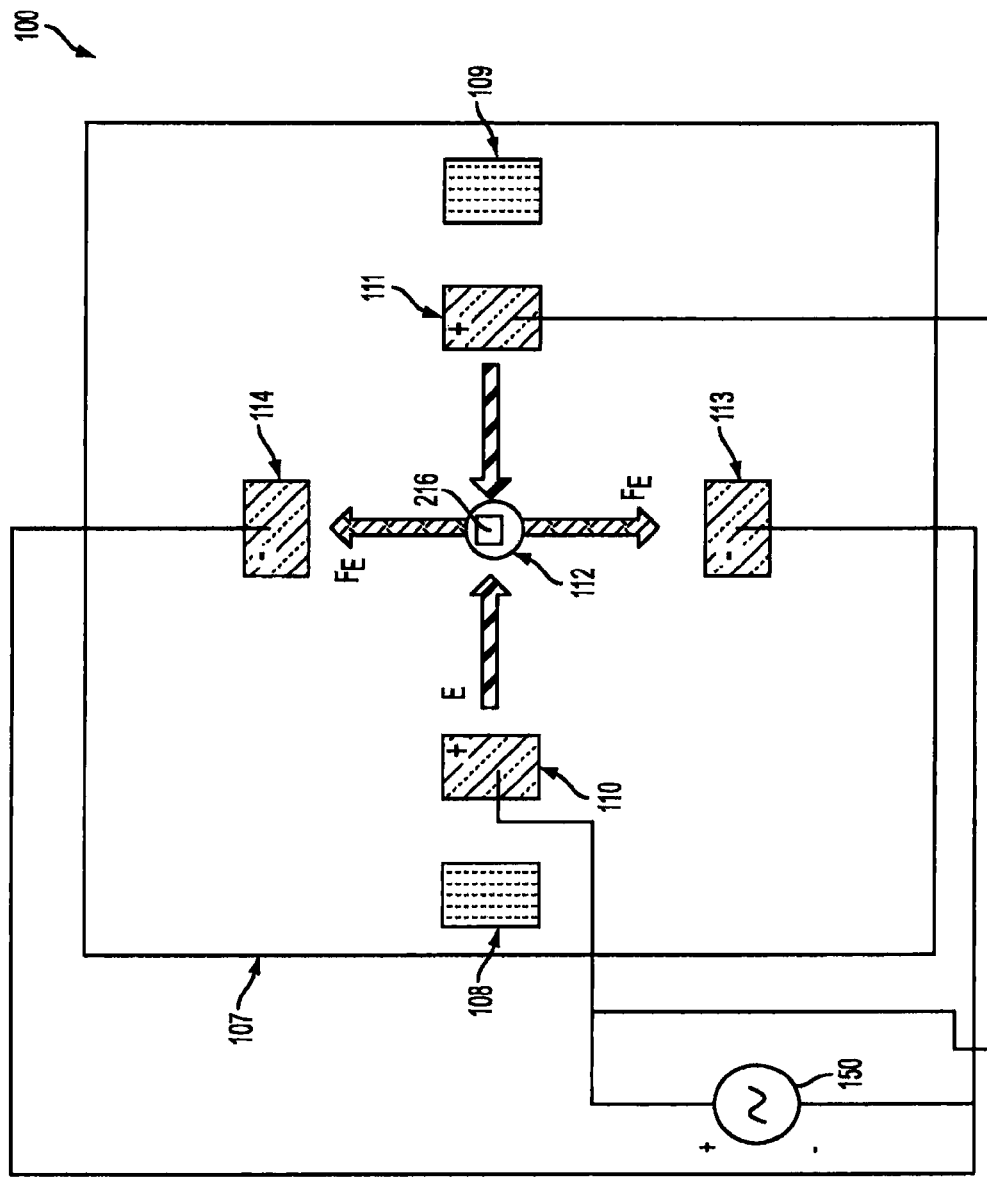
FIG. 4B illustrates how the Paul trap device positions and centers the molecule when voltage is applied with another polarity of the alternating current voltage source.

FIGS. 4A and 4B further illustrate how the Paul trap device positions and centers the molecule 216 in the reservoir 213. FIGS. 4A and 4B show a simplified version of the top view (shown in FIG. 1D) of the multilayer structure 100 within the integrated system 200, and the nanopore 112 has been enlarged for better viewing. Although not shown for the sake of clarity, it is understood that missing elements from FIG. 1D and FIG. 2 are understood to be present in FIGS. 4A and 4B.

FIG. 4A illustrates that the AC voltage source 150 applies positive voltage (positive signal $$\left(+\frac{1}{2}V_{rf}\cos(\omega_{rf}t)\right)$$

to the contact pads/windows 110 and 111, while applying negative voltage (negative signal $$\left(-\frac{1}{2}V_{rf}\cos(\omega_{rf}t)\right)$$

to contact pads/windows 113 and 114. In FIG. 4A, the electric fields flow from contact pads 113 and 114 to contact pads 110 and 111 with the net effect shown by the electric field arrows E.

The forces acting upon the molecule 216 are shown by arrows $F_E$ pointing inward from the top and bottom of the page to position the molecule 216 to the centered location of the nanopore 112. The forces $F_E$ are a result of the electric field E, and the forces $F_E$ help to keep the molecule 216 at the centered location even if the molecule 216 moves around in the reservoir 213 before being captured in the nanopore 112.

FIG. 4B illustrates that the AC voltage source 150 applies negative voltage (negative signal $$\left(-\frac{1}{2}V_{rf}\cos(\omega_{rf}t)\right)$$

to contact pads/windows 113 and 114, while applying positive voltage (positive signal $$\left(+\frac{1}{2}V_{rf}\cos(\omega_{rf}t)\right)$$

to the contact pads/windows 110 and 111. In FIG. 4B, the electric fields flow from contact pads 110 and 111 to contact pads 113 and 114 with the net effect shown by the electric field arrows E.

In this case, the forces acting upon the molecule 216 are shown by arrows $F_E$ both pointing outward to the top and bottom of the page to position the molecule 216 to the centered location of the nanopore 112.

The constant forces FE shown in both FIGS. 4A and 4B (as the AC voltage of AC voltage source 150 alternates) center/hold the molecule 216 at the centered location of the nanopore 112 (even against thermal motion and agitation), for capture in the nanopore 112. Voltage of voltage source 220 can draw the positioned molecule 216 into the nanopore 112 for sequencing, and the AC voltage of AC voltage source 150 can be applied during sequencing of the molecule 216 to hold the molecule 216 in place (although the voltage source 220 is turned off during sequencing so that the molecule 216 does not traverse through the nanopore 112 until it is time to sequence the next base 217).

FIG. 5 illustrates an example of a computer 500 (e.g., as part of the computer setup for testing and analysis) which may implement, control, and/or regulate the AC voltage of the voltage source 150, the voltage of the voltage source 220, voltage of the voltage source 221, and measurements of the ammeter in the integrated system 200 as discussed herein.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, connectors, etc.). Input/output device 570 (having proper software and hardware) of computer 500 may include and/or be coupled to the nanodevices and structures discussed herein via cables, plugs, wires, electrodes, patch clamps, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A system for capturing a molecule, the system comprising:
   a nanopore device comprising a nanopore;
   a Paul trap device integrated with the nanopore device to form an integrated system, in which an alternating voltage is applied to the Paul trap device in an electrically conductive solution to generate electric fields;
   wherein forces from the electric fields of the Paul trap device position the molecule to the nanopore in the nanopore device; and
   wherein the nanopore device is configured in which a first voltage is applied to capture the molecule in the nanopore of the nanopore device; and
   a first insulating layer disposed on top of a substrate, a first conductive layer disposed on top of the first insulating layer, a second insulating layer disposed on top of the first conductive layer, a second conductive layer disposed on top of the second insulating layer, and a third insulating layer disposed on top of the second conductive layer;
   wherein a first pair of contact pads and a second pair of contact pads are each formed on the second conductive layer, the alternating voltage alternating polarity between the first pair of contact pads and the second pair of contact pads; and
   wherein the first pair of contact pads correspond to first windows opened through the third insulating layer stopping on the second conductive layer, the first windows being positioned on opposites sides of the nanopore.

2. The system of claim 1, wherein a second voltage is applied to sequencing pads of the nanopore device to sequence bases of the molecule in the nanopore;
   wherein the second pair of contact pads correspond to second windows opened through the third insulating layer stopping on the second conductive layer, the second windows being positioned on opposites sides of the nanopore;
   wherein the sequencing pads correspond to sequencing windows opened through the third insulating layer, the second conductive layer, the second insulating layer, stopping on the first conductive layer.

3. The system of claim 1, wherein the alternating voltage is applied to the Paul trap device prior to applying the first voltage to the nanopore device.

4. The system of claim 1, wherein the alternating voltage is applied to the Paul trap device while applying the first voltage to the nanopore device.

5. The system of claim 1, wherein the molecule is centered to a location of the nanopore in the nanopore device by a combination of the forces of the Paul trap device and the first voltage applied by the nanopore device.

6. The system of claim 1, wherein the electrically conductive solution fills two reservoirs connected by the nanopore; and
   wherein insulating material surrounds immersed parts of the first pair of contact pads and the second pair of contact pads in the electrically conductive solution to prevent the first pair of contact pads and the second pair of contact pads from conducting electricity through the electrically conductive solution.

7. The system of claim 6, wherein applying the alternating voltage to the first pair of contact pads and the second pair of contact pads positions the molecule to the nanopore in one of the two reservoirs for capture in the nanopore; and
   wherein the forces, continuously changing, act upon the molecule to force the molecule into an equilibrium position centered with the nanopore, in order to prevent the molecule from being moved out of position.

8. The system of claim 6, wherein the first voltage is applied to one electrode in one of the two reservoirs and another electrode in another one of the two reservoirs.

9. The system of claim 7, wherein the first voltage moves the molecule through the nanopore for sequencing respective bases of the molecule; and
   wherein the first voltage is turned off to sequence one base and turned on again to move to a next base.

* * * * *